United States Patent
Hogenkamp et al.

(10) Patent No.: US 7,078,426 B2
(45) Date of Patent: Jul. 18, 2006

(54) ARYL SUBSTITUTED PYRAZOLES, TRIAZOLES, AND TETRAZOLES, AND THE USE THEREOF

(75) Inventors: Derk J. Hogenkamp, Carlsbad, CA (US); Phong Nguyen, Placentia, CA (US); Ji Yang, Plainsboro, NJ (US)

(73) Assignee: Euro-Celtique S.A., Luxembourg (LU)

( * ) Notice: Subject to any disclaimer, the term of this patent is extended or adjusted under 35 U.S.C. 154(b) by 1082 days.

(21) Appl. No.: 09/814,123

(22) Filed: Mar. 22, 2001

(65) Prior Publication Data

US 2002/0006947 A1 Jan. 17, 2002

Related U.S. Application Data

(60) Provisional application No. 60/191,757, filed on Mar. 24, 2000.

(51) Int. Cl.
*A61K 31/4155* (2006.01)
*C07D 231/10* (2006.01)

(52) U.S. Cl. .................................. 514/407; 548/374.1
(58) Field of Classification Search ................ 548/252, 548/255, 267.2, 267.8, 375.1, 374.1, 377.1; 514/381, 383, 406, 407
See application file for complete search history.

(56) References Cited

U.S. PATENT DOCUMENTS

| | | | | |
|---|---|---|---|---|
| 3,049,438 A | | 8/1962 | Buell et al. ................. | 117/33.5 |
| 3,058,989 A | | 10/1962 | Buell et al. ................. | 260/296 |
| 4,072,498 A | | 2/1978 | Moon et al. .................... | 71/92 |
| 4,394,514 A | | 7/1983 | Kruse ........................ | 548/508 |
| 4,454,337 A | | 6/1984 | Kruse ........................ | 560/22 |
| 4,618,681 A | * | 10/1986 | Kadaba et al. ............... | 546/276 |
| 4,639,266 A | | 1/1987 | Heubach et al. ............... | 71/92 |
| 4,962,011 A | | 10/1990 | Aldag et al. ................. | 430/281 |
| 5,134,142 A | | 7/1992 | Matsuo et al. ............... | 514/255 |
| 5,602,156 A | | 2/1997 | Kohn et al. .................. | 514/359 |
| 5,607,956 A | * | 3/1997 | Boar et al. ................... | 514/365 |
| 5,670,533 A | | 9/1997 | Matsuo et al. ............... | 514/106 |
| 5,744,492 A | | 4/1998 | Kohn et al. .................. | 514/359 |
| 6,057,346 A | | 5/2000 | Kohn et al. .................. | 514/359 |

FOREIGN PATENT DOCUMENTS

| | | |
|---|---|---|
| DE | 19 36 760 | 1/1970 |
| DE | 29 10 330 A1 | 10/1980 |
| EP | 0 273 528 A1 | 7/1988 |
| EP | 0 323 841 A2 | 7/1989 |
| EP | 0 323 841 A3 | 9/1990 |
| EP | 0 488 959 A2 | 6/1992 |
| EP | 0 323 841 B1 | 8/1993 |
| EP | 0554829 * | 8/1993 |
| EP | 1 081 146 A1 | 3/2001 |
| GB | 2 105 327 A | 3/1983 |
| JP | 11 199566 A | 7/1999 |
| WO | WO 96/11911 | 4/1996 |
| WO | WO 97/07102 | 2/1997 |
| WO | WO 99/62885 | 12/1999 |
| WO | WO 00/57877 | 10/2000 |

OTHER PUBLICATIONS

Arient, J. and Dvořák, J., "Triphenylmethane dyes. II. Introduction of the triazole group into the triphenylmethane skeleton," *Chem. Abstracts* 52:Abstract No. 12401i, The American Chemical Society (1958).

Baud, J., et al., "CGP 31358 binds to a site on the NMDA receptor that is coupled to both the transmitter recognition site and the channel domain," *Neurosci. Lett.* 107:184–188, Elsevier Scientific Publishers Ireland Ltd. (1989).

Bensimon, G., et al., "A Controlled Trial of Riluzole in Amyotrophic Lateral Sclerosis," *New Eng. J. Med.* 330:585–591, Massachusetts Medical Society (1994).

Brown, J.B. and Stammers, D.W., "Yellow color images by silver and dye bleaching," *Chem. Abstracts* 57:Abstract No. 12673d, The American Chemical Society (1962).

Brown, C.M., et al., "Neuroprotective properties of lifarizine compared with those of other agents in a mouse model of focal cerebral ischaemia," *Br. J. Pharmacol.* 115:1425–1432, Stockton Press (Aug. 1995).

Buchan, A.M., et al., "AMPA Antagonists: Do They Hold More Promise for Clinical Stroke Trials Than NMDA Antagonists," *Suppl. I Stroke* 24:148–152, Lippincott Williams and Wilkins (1993).

Catterall, W.A., "Structure and Function of Voltage–Sensitive Ion Channels," *Science* 242:50–61, American Association for the Advancement of Science (1988).

(Continued)

*Primary Examiner*—Joseph K. McKane
*Assistant Examiner*—Golam M M Shameem
(74) *Attorney, Agent, or Firm*—Sterne, Kessler, Goldstein & Fox

(57) ABSTRACT

This invention relates to compounds having the Formula I:

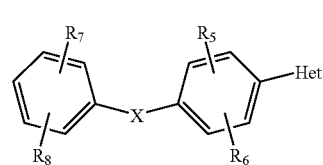

or a pharmaceutically acceptable salt, prodrug or solvate thereof, wherein Het and $R_5$–$R_8$ are set in the specification. The invention also is directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

21 Claims, 1 Drawing Sheet

OTHER PUBLICATIONS

Catterall, W.A., "Neurotoxins That Act on Voltage–Sensitive Sodium Channels in Excitable Membranes," *Ann. Rev. Pharmacol. Toxicol* 20:15–43, Annual Reviews Inc. (1980).

Catterall, W.A., "Common modes of drug action on $Na^+$ channels: local anesthetics, antiarrhythmics and anticonvulsants," *Trends Pharmacol. Sci.* 8:57–65, Elsevier Science Publishers B.V. (1987).

Cocco, M.T., et al., "Phytotoxic Activity in Pyrazole Derivatives II," *Il Farmaco Ed. Sc.* 40:272–284, Societa Italiana Di Scienze Farmaceutiche (1985).

Creveling, C.R., et al., "Batrachotoxin–Induced Depolarization and $[^3H]$ Batrachotoxinin–A $20\alpha$–Benzoate Binding in a Vesicular Preparation from Guinea Pig Cerebral Cortex," *Mol. Pharmacol.* 23:350–358, The American Society for Pharmacology and Experimental Therapeutics (1983).

Dal Monte, D. and Veggetti, P., "Derivatives of pyrazolone and pyrazolyl carbamates," *Chem. Abstracts* 53:Abstract No. 8122f, The American Chemical Society (1959).

Denicoff, K.D. et al., "Efficacy of Carbamazepine Compared With Other Agents: A Clinical Practice Survey," *J. Clin. Psychiatry* 55:70–76, Physicians'Postgraduate Press, Inc. (1994).

Dimmock, J.R., et al., "Evaluation of the thiosemicarbazones of some aryl alkyl ketones and related compounds for anticonvulsant activities," *Eur. J. Med. Chem.* 26:529–534, Elsevier Science (1991).

Donaldson, I., "Tegretol: A double blind trial in tinnitus," *J. Laryngol. Otol.* 95:947–951, Royal Society of Medicine Press (1981).

Filer, C.N., "Chapter 6, The Preparation and Characterization of Tritiated Neurochemicals," *In*:Isotopes in the Physical and Biomedical Sciences, vol. 1, Labelled Compounds (Part A), Buncel, E. and Jones, J.R. eds., pp.156–192, Elsevier Science Publishers B.V. (1987).

J.R. Geigy A.–G., "Diazo dyes," *Chem. Abstracts* 60:Abstract No. 12144b, The American Chemical Society (1964).

Graham, S.H., et al., "Neuroprotective Effects of a Use–Dependent Blocker of Voltage–Dependent Sodium Channels, BW619C89, in Rat Middle Cerebral Artery Occlusion," *J. Pharmacol. Exp. Ther.* 269:854–859, The American Society for Pharmacology and Experimental Therapeutics (1994).

Graham, S.H., et al., "A Dose–Response Study of Neuroprotection Using the AMPA Antagonist NBQX in Rat Focal Cerebral Ischemia," *J. Pharmacol. Exp. Ther.* 276:1–4, The American Society for Pharmacology and Experimental Therapeutics (1996).

Hamill, O.P., et al., "Improved Patch–Clamp Techniques for High–Resolution Current Recording from Cells and Cell–Free Membrane Patches," *Pflügers Arch.* 391:85–100, Springer–Verlag (1981).

Hunskaar, S. et al.,"Formalin test in mice, a useful technique for evaluating mild analgesics," *J. Neurosci. Methods* 14:69–76, Elsevier Science Publishers B.V.(1985).

Iwasaki, Y., et al., "CNQX prevents spinal motor neuron death following sciatic nerve transection in newborn rats," *J. Neurosci.* 134:21–25, Elsevier Science B.V. (1995).

Kuo, C.–C. and Bean, B.P., "Slow Binding of Phenytoin to Inactivated Sodium Channels in Rat Hippocampal Neurons," *Mol. Pharmacol.* 46:716–725, The American Society for Pharmacology and Experimental Therapeutics (1994).

Lam, P.Y.S., et al., "New Aryl/Heteroacryl C–N Bond Cross–coupling Reactions via Arylboronic Acid/Cupric Acetate Arylation," *Tetrahedron Lett.* 39:2941–2944, Elsevier Science Ltd. (1998).

Majumdar, B., et al., "An electrocochleographic study of the effects of lignocaine on patients with tinnitus," *Clin. Otolaryngol* 8:175–180, Blackwell Scientific Publications (1983).

Magagnoli, R., "1–(p–Benzoylphenyl)–3–alkyl(or benzamido)–5–pyrazolones as color couplers," *Chem. Abstracts* 65:Abstract No. 5576g, The American Chemical Society (1966).

Møller, A.R., "Similarities Between Chronic Pain and Tinnitus," *Am. J. Otol.* 18:577–585, Lippincott–Raven Publishers (1997).

Neeff, R., "Anilinoanthraquinone dyes," *Chem. Abstracts* 63:Abstract No. 11745g, The American Chemical Society (1965).

Ohizumi, Y., et al., "Specific Inhibition of $[^3H]$ Saxitoxin Binding to Skeletal Muscle Sodium Channels by Geographutoxin II, a Polypeptide Channel Blocker," *J. Biol. Chem.* 261:6149–6152, The American Society of Biological Chemists, Inc. (1986).

Pokornỳ, M. and Haase, J., "Substantive triphenodioxazine dyes containing a naphtho–[1,2–d] triazole nucleus," *Chem. Abstracts* 55:Abstract No. 7854i, The American Chemical Society (1961).

Polevoi, L.G., et al., "Relation of aminopyrazole structures to their neurotropic activity," retrieved from STN, Database Accession No. 69:1557 CAPLUS, Chemical Abstracts Service (1968).

Ragsdale, D.S., et al., "Frequency and Voltage–Dependent Inhibition of Type IIA $Na^+$ Channels, Expressed in a Mammalian Cell Line, by Local Anesthetic, Antiarrhythmic, and Anticonvulsant Drugs," *Mol. Pharmacol.* 40:756–765, Williams & Wilkins (1991).

Rasavi, D., "Reactive dyes," *Chem. Abstracts* 59:Abstract 6555g, The American Chemical Society (1963).

Sheardown, M.J., et al., "AMPA, but not NMDA, receptor antagonism is neuroprotective in gerbil global ischaemia, even when delayed 24 h," *Eur. J. Pharmacol.* 236:347–353, Elsevier Science Publishers B.V. (1993).

Simpson, J.J., and Davies, W.E., "Recent advances in the pharmacological treatment of tinnitus," *Trends Pharmacol. Sci.* 20:12–18, Elsevier Science London (1999).

Steck, E.A., et al., "Some Guanazole Derivatives," *J. Am. Chem. Soc.* 80:3929–3931, The American Chemical Society (1958).

Steck, E.A., and Nachod, F.C., "Absorption Spectra of Heterocyclic Compounds. VII. Some 3(2H)–Pyridazones," *J. Am. Chem. Soc.* 79:4408–4411, The American Chemical Society (1957).

Stefancich, G., et al., "Analogues of Bifonazole with Two Imidazole Moieties and Related Azoles," *Arch. Pharm. (Weinheim)* 323:273–280, VCH Verlagsgesellschaft mbH (1990).

Stys, P.K., et al., "Ionic Mechanisms of Anoxic Injury in Mammalian CNS White Matter: Role of $Na^+$ Channels and $Na^+$–$Ca^{2+}$ Exchanger," *J. Neurosci.* 12:430–439, Society for Neuroscience (1992).

Taylor, C.P., and Meldrum, B.S., "$Na^+$ channels as targets for neuroprotective drugs," *Trends Pharmacol. Sci.* 16:309–316, Elsevier Trends Journals (1995).

Tonndorf, J., "The analogy between tinnitus and pain: A suggestion for a physiological basis of chronic tinnitus," *Hear Res.* 28:271–275, Elsevier Science Publishers B.V. (1987).

Verndoorn, T.A., et al., "Functional Properties of Recombinant Rat $GABA_A$ Receptors Depend upon Subunit Composition," *Neuron* 4:919–928, Cell Press (1990).

Wrathall, J.R., et al., "Amelioration of Functional Deficits from Spinal Cord Trauma with Systemically Administered NBQX, an Antagonist of Non–N–methyl–D–aspartate receptors," *Exp. Neurol.* 137:119–126, Academic Press, Inc. (1996).

Zweidler, R. and Keller, E., "Fluorescent ditriazole compounds," *Chem. Abstracts 52*:Abstract No. 8206c, The American Chemical Society (1958).

Dialog File 351, Accession No. 669110, Derwent WPI English Language abstract for DE 19 36 760 (Document AL1).

Dialog File 351, Accessin No. 2553655, Derwent WPI English language abstract for DE 29 10 330 A1 (Document AM1).

Dialog File 351, Accession No. 12667941, Derwent WPI English Language abstract for JP 11 199566 A (Document AL3).

International Search Report for International Application No. PCT/US 01/08972, mailed Sep. 24, 2001.

* cited by examiner

ARYL SUBSTITUTED PYRAZOLES, TRIAZOLES, AND TETRAZOLES, AND THE USE THEREOF

This application claims the priority benefit under 35 U.S.C. §119 of U.S. Provisional Application No. 60/191,757, filed Mar. 24, 2000, the entirety of which is incorporated by reference herein.

BACKGROUND OF THE INVENTION

1. Field of the Invention

This invention is in the field of medicinal chemistry. In particular, the invention relates to aryl substituted pyrazoles, triazoles and tetrazoles, and the discovery that these compounds are anticonvulsants and act as blockers of sodium ($Na^+$) channels.

2. Related Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., *Trends Pharmacol. Sci.* 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., *J Pharmacol. Exp. Ther.* 269:854–859 (1994); Brown et al., *British J Pharmacol.* 115:1425–1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J. Neurosci.* 12:430–439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensim et al., *New Engl. J. Med.* 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309–316 (1995)), and carbamazepine and lamotrigine have been used for the treatment of manic depression (Denicott et al., *J. Clin. Psychiatry* 55: 70–76 (1994)). Furthermore, based on a number of similarities between chronic pain and tinnitus (Moller, A. R. *Am. J. Otol.* 18: 577–585 (1997); Tonndorf, *J. Hear. Res.* 28: 271–275 (1987)) it has been proposed that tinnitus should be viewed as a form of chronic pain sensation (Simpson, J. J. and Davies, E. W. *Tip.* 20: 12–18 (1999)). Indeed, lignocaine and carbamazepine have been shown to be efficacious in treating tinnitus (Majumdar, B. et al. *Clin. Otolaryngol.* 8: 175–180 (1983); Donaldson, I. *Laryngol. Otol.* 95: 947–951 (1981)).

It has been established that there are at least five to six sites on the voltage-sensitive $Na^+$ channels which bind neurotoxins specifically (Catterall, W. A., *Science* 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15–43 (1980)).

Cocco, M. T.; Maccioni, A.; Plumitallo, A.; *Farmaco Ed.Sci.*, 40: 1985; 272–284 describe the two following compounds:

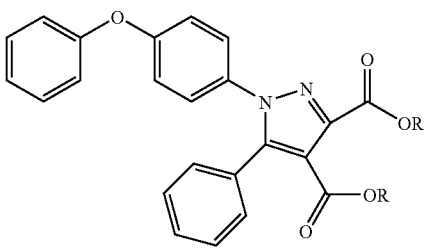

R = H, Et

Other aryl substituted heterocycles are described in Stefancich, G. et al. *Arch.Pharm.(Weinheim Ger.)* 323: 273–280 (1990) as antimycotic agents. These compounds are described in Appendix A.

Compounds of Formula I have not been used heretofor for treating a disorder responsive to the blockade of sodium channels in a mammal.

SUMMARY OF THE INVENTION

The present invention is related to the discovery that aryl substituted pyrazoles, triazoles and tetrazoles represented by Formula I act as blockers of sodium ($Na^+$) channels.

The invention is also related with treating a disorder responsive to the blockade of sodium channels in a mammal suffering from excess activity of said channels by administering an effective amount of a compound of Formula I as described herein.

A further aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthesics, antiarrhythmics, and treating tinnitus by administering a compound of Formula I to a mammal in need of such treatment.

Another aspect of the present invention is directed to the use of the compounds of Formula I as blockers of sodium channels.

The present invention is also directed to the use of a compound of Formula I for the treatment of neuronal damage following global and focal ischemia, and for the treatment or prevention of neurodegenerative conditions, such as amyotrophic lateral sclerosis (ALS), for the treatment of tinnitus, as antimanic depressants, as local anesthetics, as antiarrhythmics, as anticonvulsants and for the treatment or prevention of diabetic neuropathy and for the treatment of pain including both acute and chronic pain and migraine headache.

A further aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

A number of compounds useful in the present invention have not been heretofor reported. Thus, the present invention is also directed to novel aryl substituted pyrazoles, triazoles and tetrazoles of Formula I.

Further, the present invention is directed to $^3H$ and $^{14}C$ radiolabeled compounds of Formula I and their use as radioligands for their binding site on the sodium channel.

Additional embodiments and advantages of the invention will be set forth in the description which follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1A: IV-curves, FIG. 1C: steady-state inactivation, FIG. 1B: repriming kinetics.

DETAILED DESCRIPTION OF THE INVENTION

Figure 1A:
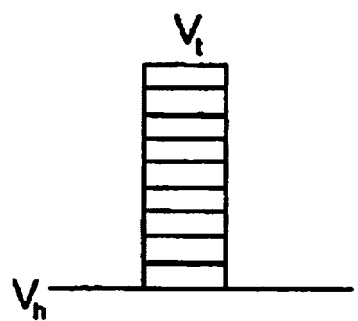
FIGS. 1A, 1B, 1C, and 1C are voltage pulse protocols used to assess the potency and kinetics of inhibition of the $Na^+$ channels by the compounds as follows.

The present invention arises out of the discovery that the aryl substituted pyrazoles, triazoles and tetrazoles of Formula I act as blockers of $Na^+$ channels. In view of this discovery, compounds of Formula I are useful for treating disorders responsive to the blockade of sodium ion channels.

The compounds useful in this aspect of the present invention are the aryl substituted pyrazoles, triazoles and tetrazoles represented by Formula I:

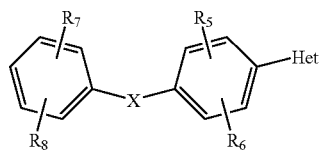

I or a pharmaceutically acceptable salt, prodrug or solvate thereof, wherein

X is one of O, S, $NR_9$, $CH_2$, $NR_9C(O)$, or $C(O)NR_9$ where $R_9$ is hydrogen or $C_1$–$C_{10}$ alkyl;

Het is a heteroaryl selected from the group consisting of

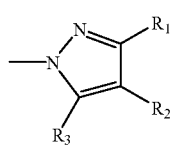

(i)

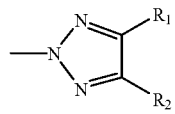

(ii)

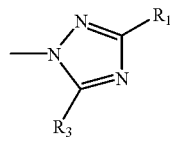

(iii)

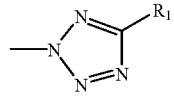

(iv)

$R_1$ is selected from the group consisting of hydrogen, optionally substituted alkyl, optionally substituted heteroaryl, $C(O)R_{10}$, $CH_2C(O)R_{10}$, $S(O)R_{10}$, and $SO_2R_{10}$;

$R_2$ and $R_3$ are independently selected from the group consisting of hydrogen, alkyl, alkenyl, alkynyl, aryl, cyano, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, aminosulfonyl, alkylaminosulfonyl, and alkylsulfonyl;

$R_5$, $R_6$, $R_7$, and $R_8$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol;

$R_{10}$ is selected from the group consisting of amino, alkyl, alkenyl, alkynyl, $OR_{11}$, alkylamino, dialkylamino, alkenylamino, dialkylaminoalkenyl, cycloalkyl, aryl, heterocycle, heteroaryl, aralkyl, arylalkenyl, arylalkynyl, and cycloalkylalkylamino;

$R_{11}$ is selected from the group consisting of hydrogen, optionally substituted alkyl, and an alkalimetal.

Thus, the present invention is directed to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthesics, antiarrhythmics, and treating tinnitus by administering a compound of Formula I to a mammal in need of such treatment.

The present invention is also directed to novel compounds having Formula I as described above; provided that:

1) when Het is (ii), and X is O, then $R_{10}$ is not alkyl, aralkyl, aryl, or $OR_{11}$;
2) when Het is (i) or (ii), then X is not $NR_9$;
3) when Het is (iii), then X is not $CH_2$; and
4) when Het is (iii), and X is O, then $R_{10}$ is not $OR_{11}$.

Optional substituents on optionally substituted groups, when not otherwise defined, include one or more groups independently selected from the group consisting of halo, halo($C_{1-6}$) alkyl, aryl, pyrimidine, cycloalkyl, $C_{1-6}$ alkyl, $C_{2-6}$ alkenyl, $C_{2-6}$ alkynyl, aryl($C_{1-6}$)alkyl, aryl($C_{2-6}$) alkenyl, aryl($C_{2-6}$)alkynyl, cycloalkyl($C_{1-6}$)alkyl, hydroxy ($C_{1-6}$)alkyl, amino($C_{1-6}$)alkyl, carboxy($C_{1-6}$)alkyl, alkoxy ($C_{1-6}$)alkyl, nitro, amino, ureido, cyano, $C_{1-6}$ acylamino, hydroxy, thiol, $C_{1-6}$ acyloxy, azido, $C_{1-6}$ alkoxy, carboxy, aminocarbonyl, carbamoyloxy, $C_{1-6}$ alkylsulfonylamino, $C_{1-6}$ acyl, and $C_{1-6}$ alkylthiol groups mentioned above as long as the resulting compound is stable. Preferred optional substituents include: halo, halo($C_{1-6}$)alkyl, hydroxy($C_{1-6}$) alkyl, amino($C_{1-6}$)alkyl, hydroxy, nitro, $C_{1-6}$ alkyl, $C_{1-6}$ alkoxy, aminocarbonyl, carbamoyloxy, $C_{1-6}$ alkylsulfonylamino, $C_{1-6}$ acyl and amino.

Preferably, $R_1$ is selected from the group consisting of an alkyl optionally substituted by halogen, hydroxy, carbamoyloxy, $C_{1-6}$ acyl, $C_{1-6}$ alkylsulfonylamino, aryl, preferably phenyl, or aminocarbonyl; C(O)$R_{10}$; CH$_2$C(O) $R_{10}$; or SO$_2R_{10}$, wherein $R_{10}$ is selected from the group consisting of $C_{1-6}$ alkyl, $C_{2-6}$ alkenyl, OR$_{11}$, amino, $C_{1-6}$ alkylamino, di($C_{1-6}$)alkylamino, $C_{2-6}$ alkenylamino, heterocycle and mono- and di-($C_{1-6}$)alkylaminoalkenyl, and wherein $R_{11}$ is as defined above.

Preferably, $R_{10}$ is selected from the group consisting of $C_{1-6}$ alkyl, $C_{2-6}$ alkenyl, OR$_{11}$, amino, $C_{1-6}$ alkylamino, di($C_{1-6}$)alkylamino, $C_{2-6}$ alkenylamino, mono- and di-($C_{1-6}$)alkylamino($C_{2-6}$)alkenyl, N-morpholinyl, N-pyrrolidinyl, and N-piperazinyl, all of which can be optionally substituted, wherein $R_{11}$ is as defined above.

Preferably, $R_2$ and $R_3$ are independently selected from the group consisting of hydrogen, $C_1$–$C_6$ alkyl, $C_2$–$C_6$ alkenyl, $C_2$–$C_6$ alkynyl, amino($C_1$–$C_6$)alkyl, amino, cyano, $C_1$–$C_6$ alkoxy, $C_1$–$C_6$ alkylthio, $C_1$–$C_6$ alkylsulfinyl, hydroxy ($C_1$–$C_6$)alkyl, alkoxy($C_1$–$C_6$)alkyl, carboxy($C_1$–$C_6$)alkyl, aminocarbonyl, $C_1$–$C_6$ alkylaminocarbonyl, $C_6$–$C_{10}$ arylaminocarbonyl, $C_6$–$C_{10}$ aryl($C_1$–$C_6$) alkylaminocarbonyl, $C_1$–$C_6$ alkylcarbonylamino, $C_6$–$C_{10}$ arylcarbonylamino, and $C_6$–$C_{10}$ aryl($C_1$–$C_6$) alkylcarbonylamino, more preferably hydrogen, $C_1$–$C_6$ alkyl, $C_1$–$C_6$ alkoxy, amino($C_1$–$C_6$)alkyl, $C_1$–$C_6$ alkylthio and aminocarbonyl.

The groups $R_5$–$R_8$ each take place of a hydrogen atom that would otherwise be present in any position on the aryl ring to which the R group is attached.

Preferably, $R_5$, $R_6$, $R_7$, and $R_8$ are independently selected from the group consisting of hydrogen, halo (preferably chloro or fluoro), halo($C_1$–$C_6$)alkyl, $C_1$–$C_6$ alkyl, hydroxy ($C_1$–$C_6$)alkyl, amino($C_1$–$C_6$)alkyl, carboxy($C_1$–$C_6$)alkyl, alkoxy($C_1$–$C_6$)alkyl, nitro, amino, $C_1$–$C_6$ acylamino, amide, hydroxy, thiol, $C_1$–$C_6$ acyloxy, $C_1$–$C_6$ alkoxy, carboxy, carbonylamido and $C_1$–$C_6$ alkylthiol.

One group of preferred compounds falling within the scope of Formula I include compounds wherein $R_1$ is C(O)$R_{10}$ or SO$_2R_{10}$ where $R_{10}$ is defined above, and is more preferably amino or $C_{1-6}$ alkyl. In this group of compounds, X is more preferably O or S, most preferably O.

Especially preferred in this group are compounds where $R_5$ and $R_6$ are each hydrogen; $R_2$ and $R_3$ are both H; and $R_7$ and $R_8$ are selected from the group consisting of hydrogen, halo, halo($C_1$–$C_6$)alkyl, $C_1$–$C_6$ alkyl, hydroxy($C_1$–$C_6$)alkyl, amino($C_1$–$C_6$)alkyl, carboxy($C_1$–$C_6$)alkyl, alkoxy($C_1$–$C_6$) alkyl, nitro, amino, $C_1$–$C_6$ acylamino, amide, hydroxy, thiol, $C_1$–$C_6$ acyloxy, $C_1$–$C_6$ alkoxy, carboxy, carbonylamido and $C_1$–$C_6$ alkylthiol.

Another group of preferred compounds includes compounds of Formula I:

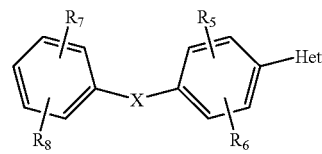

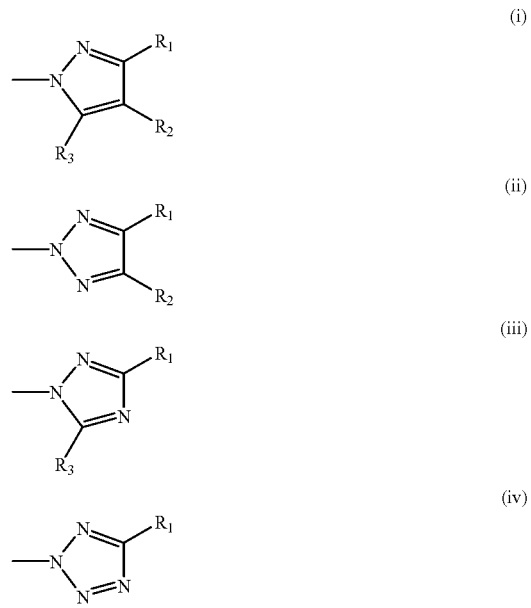

or a pharmaceutically acceptable salt, prodrug or solvate thereof, wherein

X is O or S, preferably O;

Het is a heteroaryl selected from the group consisting of preferably (i) or (iii);

$R_1$ is C(O)$R_{10}$, CH$_2$C(O)$R_{10}$, or SO$_2R_{10}$ wherein $R_{10}$ is amino, alkyl, N-morpholinyl, N-pyrrolidinyl or N-piperazinyl, more preferably amino, all of which can be optionally substituted. $R_1$ is preferably C(O)$R_{10}$, where $R_{10}$ is amino, $C_1$–$C_6$ alkyl, or a heterocycle, such as N-morpholinyl, N-pyrrolidinyl and N-piperazinyl;

$R_2$ and $R_3$ are independently hydrogen, $C_1$–$C_6$ alkyl, $C_1$–$C_6$ alkylthio or $C_1$–$C_6$ alkylsulfinyl, with $R_2$ and $R_3$ preferably being hydrogen; $R_5$ and $R_6$ are as defined above and are preferably hydrogen; and $R_7$ and $R_8$ are independently selected from the group consisting of hydrogen, halo, halo($C_1$–$C_6$)alkyl, $C_1$–$C_6$ alkyl, hydroxy($C_1$–$C_6$)alkyl, amino($C_1$–$C_6$)alkyl, carboxy ($C_1$–$C_6$)alkyl, alkoxy($C_1$–$C_6$)alkyl, nitro, amino, $C_1$–$C_6$ acylamino, amide, hydroxy, thiol, $C_1$–$C_6$ acyloxy, $C_1$–$C_6$ alkoxy, carboxy, carbonylamido and $C_1$–$C_6$ alkylthiol;

provided that:

1) when Het is (ii), and X is O, then $R_{10}$ is not alkyl, aralkyl, aryl or OR$_{11}$;
2) when Het is (iii), and X is O, then $R_{10}$ is not OR$_{11}$.

Exemplary preferred compounds that may be employed in this method of invention include, without limitation:

1-[4-(4-nitrophenoxy)phenyl]-1H-[1,2,4]triazole;

1-[4-(4-fluorophenoxy)phenyl]-3-methylpyrazole;

3-methyl-1-(4-phenoxyphenyl)pyrazole;

1-(4-phenoxyphenyl)-1H-pyrazole-3-carboxamide;
1-(4-phenoxyphenyl)-1H-pyrazole-5-carboxamide;
1-[4-(4-fluorophenoxy)phenyl]-1H-pyrazole-3-carboxamide;
1-[4-(4-nitrophenoxy)phenyl]-1H-[1,2,4]triazole-3-carboxamide; and
1-[4-(4-chloro-2-fluorophenoxy)phenyl]-1H-pyrazole-3-carboxamide.

Another group of exemplary preferred compounds that may be employed in this invention include 1-[4-(4-fluorophenoxy)phenyl]-5-methylpyrazole, 1-(4-phenoxyphenyl)-1H-pyrazole-4-carboxamide, and 4-(4-fluorophenoxy)phenylpyrazole.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, benzofuryl, pyranyl, isobenzofuranyl, benzoxazonyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, thiazolyl, isothiazolyl, phenothiazinyl, isoxazolyl, furazanyl, and phenoxazinyl groups).

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl.

Typical $C_{2-4}$ alkenyl groups include ethenyl, propenyl, isopropenyl, butenyl, and sec-butenyl.

Useful alkynyl groups are $C_{2-6}$ alkynyl groups, preferably $C_{2-4}$ alkynyl.

Typical $C_{2-4}$ alkynyl groups include ethynyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful heteroarylalkyl groups include any of the above-mentioned $C_{1-10}$ alkyl groups substituted by any of the above-mentioned heteroaryl groups.

Useful heteroarylalkenyl groups include any of the above-mentioned $C_{2-4}$ alkenyl groups substituted by any of the above-mentioned heteroaryl groups.

Useful heteroarylalkynyl groups include any of the above-mentioned $C_{2-4}$ alkynyl groups substituted by any of the above-mentioned heteroaryl groups.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

The term heterocycle is used herein to mean saturated or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperazine, morpholine, imidazoline, pyrazolidine, benzodiazepines and the like.

Useful heterocycloalkyl groups include any of the above-mentioned $C_{1-10}$ alkyl groups substituted by any of the above-mentioned heterocyclic groups.

Useful alkylamino and dialkylamino groups are —NHR$_{20}$ and —NR$_{20}$R$_{21}$, wherein R$_{20}$ and R$_{21}$ are $C_{1-10}$ alkyl groups.

Aminocarbonyl group is —C(O)NH$_2$.

Useful alkylaminocarbonyl groups are carbonyl groups substituted by —NHR$_{20}$ and —NR$_{20}$R$_{21}$, wherein R$_{20}$ and R$_{21}$ are $C_{1-10}$ alkyl groups as defined above.

Useful alkylthiol groups include any of the above-mentioned $C_{1-10}$ alkyl groups substituted by a —SH group.

Useful alkylsulfinyl groups include any of the above-mentioned $C_{1-10}$ alkyl groups attached to a sulfinyl (—SO—).

Useful alkylsulfonyl groups include any of the above-mentioned $C_{1-10}$ alkyl groups attached to a sulfonyl (—SO$_2$—).

A carbamoyloxy group is —O—C(O)—NH$_2$.
A carboxy group is —COOH.
An azido group is —N$_3$.
An ureido group is —NH—C(O)—NH$_2$.
An amino group is —NH$_2$.
An amide group is an organic radical having —NHC(O)— as a functional group.

The invention disclosed herein is meant to encompass all pharmaceutically acceptable salts thereof of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass prodrugs of the disclosed compounds. Prodrugs are considered to be any covalently bonded carriers which release the active parent drug in vivo. Examples of prodrugs include esters or amides of Formula I with $R_2$–$R_{11}$ as hydroxyalkyl or aminoalkyl, and these may be prepared by reacting such compounds with anhydrides such as succinic anhydride.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{13}$C, $^{14}$C, $^{15}$N $^{18}$O, $^{17}$O, $^{31}$P, $^{32}$P, $^{35}$S, $^{18}$F, and $^{36}$Cl, respectively.

Some of the compounds disclosed herein may contain one or more asymmetric centers and may thus give rise to enantiomers, diastereomers, and other stereoisomeric forms. The present invention is also meant to encompass racemic mixtures, resolved forms mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

Since the compounds of Formula I are blockers of sodium ($Na^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I are also useful as antitinnitus agents, antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

The invention is also directed to a method for treating disorders responsive to the blockade of sodium channels in animals suffering thereof.

Particular preferred embodiments of the aryl substituted heteroaryl compounds for use in method of this invention are represented by previously defined Formula I.

The compounds of this invention may be prepared using methods known to those skilled in the art.

The synthesis of pyrazoles of Formula I can be prepared as shown in Schemes 1 and 2. The boronic acid coupling was accomplished using the procedure of Lam, Y. S. et al. *Tetrahedron Lett.* 39. 2941–2944 (1998).

Scheme 1

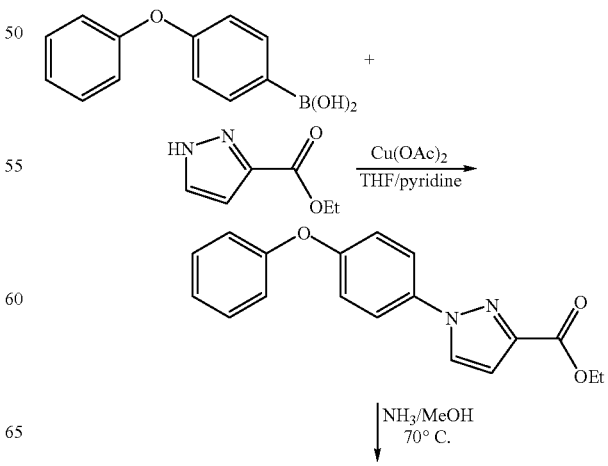

-continued

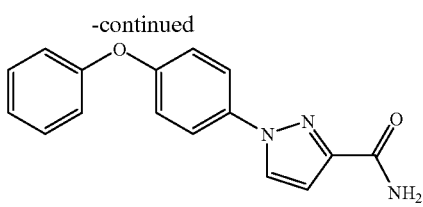

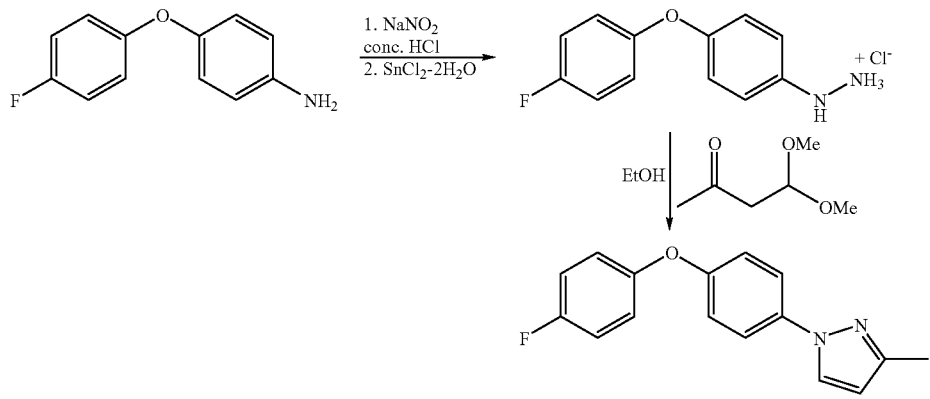

Scheme 2

30

Triazoles of Formula I can be prepared as shown in Scheme 3, employing commerically available 4-(1,2,4-triazol-1-yl)phenol (Lancaster Synthesis).

Scheme 3

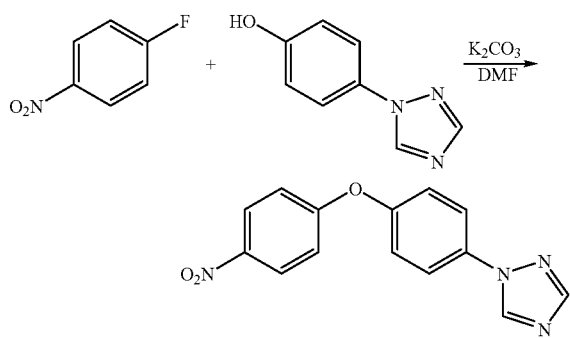

The invention is also directed to $^3$H and $^{14}$C radiolabeled compounds of Formula I and their use as radioligands for their binding site on the sodium channel. For example, one use of the labeled compounds of the invention is the characterization of specific receptor binding. Another use of the labeled compounds of the invention is an alternative to animal testing for the evaluation of structure-activity relationships. The receptor assay is performed at a fixed concentration of a labeled compound of Formula I and at increasing concentrations of a test compound in a competition assay.

Tritiated compounds of Formula I can be prepared by introducing tritium into the compound of Formula I by, for example, catalytic dehalogenation with tritium. This method includes reacting a suitably halogen-substituted precursor of a compound of Formula I with tritium gas in the presence of a suitable catalyst, for example Pd/C, in the presence or absence of a base. Other suitable methods for preparing tritiated compounds can be found in Filer, *Isotopes in the Physical and Biomedical Sciences*, Vol. 1, *Labeled Compounds (Part A)*, Chapter 6. $^{14}$C-labeled compounds can be prepared by employing starting materials having a 14C carbon.

The compounds of the present invention can be assessed by electrophysiological assays in dissociated hippocampal neurons for sodium channel blocker activity. These compounds also can be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of Na$^+$ permeability in response to depolarization associated with the action potential in many excitable cells including muscle, nerve and cardiac cells.

One aspect of the present invention is the discovery of the mechanism of action of the compounds herein described as specific Na$^+$ channel blockers. Based upon the discovery of this mechanism, these compounds are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formula I that are blockers of voltage-sensitive sodium channels. According to the present invention, those compounds having preferred sodium channel blocking properties exhibit an IC$_{50}$ of about 100 μM or less in the electrophysiological assay described herein. Preferably, the compounds of the present invention exhibit an IC$_{50}$ of 10 μM or less. Most preferably, the compounds of the present invention exhibit an IC$_{50}$ of about 1.0 μM or less. Substituted heteroaryl compounds of the present invention may be tested for their Na$^+$ channel blocking activity by the following electrophysiological and binding assays.

Electrophysiological Assay:

Cell Preparation:

HEK-293 (NaIIA-B2) cell line stably expressing the rBIIA isoform of Na$^+$ channels is established in-house. The cells are cultured using standard techniques, as described previously (Verdoorn, T. A, et al., *Neuron* 4:919–928

(1990)). For electrophysiology, cells are plated onto poly-D-lysine pre-coated Cellware 35 mm Petri dishes (BIOCOAT, Becton Dickinson) at a density of ~10$^4$ cells/dish on the day of re-seeding from confluent cultures. Our experience has been that cells are suitable for recordings for 2–3 days after plating.

Patch-clamp Recordings of Voltage-sensitive Na$^+$ Currents:

Whole-cell voltage-clamp recordings are made using conventional patch-clamp techniques (Hamill et al., *Pfluegers Arch.* 391:85–100 (1981)) with an Axopatch 200A amplifier (Axon Instruments, Foster City, Calif.). The recording chamber is continuously superfused with the external solution (150 mM NaCl, 5.4 mM KCl, 1.8 mM CaCl$_2$, 1 mM MgCl$_2$, 10 mM HEPES, 10 mM glucose, pH 7.4 adjusted with NaOH, osmolality ~320 mmol/kg) at a speed of about 1 mL/min. Recording pipettes were pulled from the thick-walled capillaries (WPI, Sarasota, Fla.) and fire-polished. The pipette resistances range from 1 to 3 MΩ when the pipettes are filled with internal solution containing (in mM): 130 CsF, 20 NaCl, 2 MgCl$_2$, 10 EGTA, 10HEPES, pH adjusted to 7.4 with CsOH, osmolality ~310 mmol/kg. Drugs and intervening wash-outs are applied through a linear array of flow pipes (Drummond Microcaps, 2 µL, 64-mm length). Compounds are dissolved in dimethylsulfoxide (DMSO) to make a 30 mM stock solution, which is subsequently diluted into the external solution to give final concentrations of 0.1–100 µM. At the highest (1%) concentration, DMSO inhibits the size of Na$^+$ current only slightly. Currents are recorded at room temperature (22–25° C.), filtered at 3 kHz with an active 8-pole Bessel filter (Frequency Devices, Haverhill, Mass.), digitized at 10–50 µs intervals, and stored using Digidata 1200 analog/digital interface with Pclamp6/Clampex software (Axon Instruments). Series resistance is cancelled typically by ~75% when necessary.

Figure 1B:
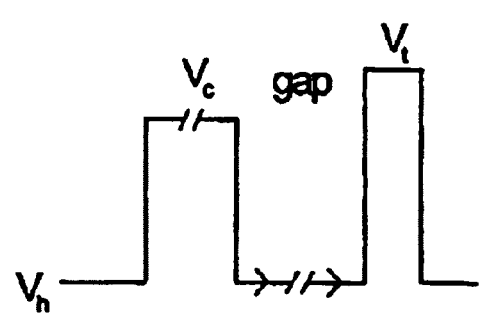
Figure 1C:
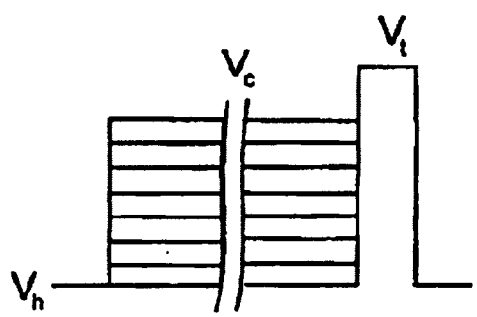
Figure 1D:
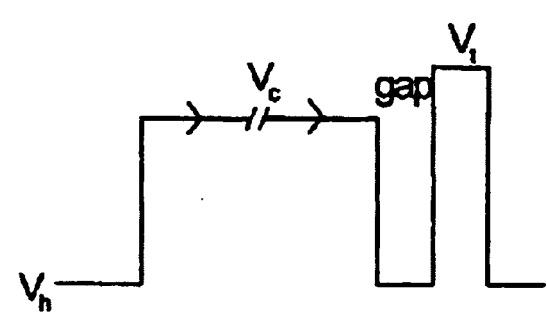
FIG. 1D: time course of binding.

The following voltage pulse protocols A, B, C, and D are used to assess the potency and kinetics of inhibition of the Na$^+$ channels by the compounds (FIGS. 1A–1D). Current-voltage relationship (IV-curve), protocol A, is used to report the voltage at which the maximal inward Na$^+$ current is achieved. This voltage is used throughout the experiment as testing voltage, $V_t$. The steady-state inactivation (or, availability) curve, protocol C, is used to get the voltage at which almost complete (≧95%) inactivation of Na$^+$ channels occurs; it serves as voltage for conditioning prepulse, $V_c$, throughout the experiment. Protocol B reports how fast the channels recover from inactivation at hyperpolarized voltages. This permits us to set up the duration of the hyperpolarization gap which is used in measurement of the kinetics of binding of compounds to inactivated Na$^+$ channels (protocol D). Channel repriming under control conditions is fast (≧90% recovery during first 5–10 ms). If a drug substantially retards the repriming process, then it becomes possible (protocol D) to accurately measure the kinetics of binding of the inhibitor to inactivated channels as well as the steady-state affinity ($k_+$ and $K_i$). To estimate $k_+$ values, the reduction in peak currents in successive trials with varying pre-pulse duration is plotted as a function of pre-pulse duration and the time constant (τ) measured by mono-exponential fit. A plot of 1/τ as a function of antagonist concentration then allows calculating of the macroscopic binding rates of the antagonists. To determine $K_i$ values the partial inhibition curves measured by fractional responses in steady-state are fitted with the logistic equation:

$$I/I_{control} = 1/(1+([\text{antagonist}]/K_i)^p),\quad \text{Eq. 2}$$

where $I_{control}$ is the maximal Na$^+$ current in the absence of antagonist, is the drug concentration, $K_i$ is the concentration of antagonist that produces half maximal inhibition, and p is the slope factor.

In vitro Binding Assay:

The ability of compounds of the present invention to modulate either site 1 or site 2 of the Na$^+$ channel is determined following the procedures fully described in Yasushi, *J. Biol. Chem.* 261:6149–6152 (1986) and Creveling, *Mol. Pharmacol.* 23:350–358 (1983), respectively. Rat forebrain membranes are used as sources of Na$^+$ channel proteins. The binding assays are conducted in 130 µM choline chloride at 37° C. for 60-minute incubation with [3] saxitoxin and [$^3$H] batrachotoxin as radioligands for site 1 and site 2, respectively.

In vivo Pharmacology:

The compounds of the present invention may be tested for in vivo anticonvulsant activity after i.v., p.o. or i.p. injection using a number of anticonvulsant tests in mice, including the maximum electroshock seizure test (MES). Maximum electroshock seizures are induced in male NSA mice weighing between 15–20 g and male Sprague-Dawley rats weighing between 200–225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results are treated in a quantal manner.

The compounds may be tested for their antinociceptive activity in the formalin model as described in Hunskaar, S., O. B. Fasmer, and K. Hole, *J. Neurosci. Methods* 14. 69–76 (1985). Male Swiss Webster NIH mice (20–30 g; Harlan, San Diego, Calif.) are used in all experiments. Food is withdrawn on the day of experiment. Mice are placed in Plexiglass jars for at least 1 hour to accommodate to the environment. Following the accommodation period mice are weighed and given either the compound of interest administered i.p. or p.o., or the appropriate volume of vehicle (10% Tween-80). Fifteen minutes after the i.p. dosing, and 30 minutes after the p.o. dosing mice are injected with formalin (20 µL of 5% formaldehyde solution in saline) into the dorsal surface of the right hind paw. Mice are transferred to the Plexiglass jars and monitored for the amount of time spent licking or biting the injected paw. Periods of licking and biting are recorded in 5 minute intervals for 1 hour after the formalin injection. All experiments are done in a blinded manner during the light cycle. The early phase of the formalin response is measured as licking/biting between 0–5 mm, and the late phase is measured from 15–50 min. Differences between vehicle and drug treated groups are analyzed by one-way analysis of variance (ANOVA). A P value ≦0.05 is considered significant. Having activity in blocking the acute and second phase of formalin-induced paw-licking activity, the compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200–225 g are anesthetized with halothane (1–3% in a mixture of 70% air and 30% oxygen) and their body temperature is controlled during anesthesia through use of a homeothermic blanket. A 2-cm dorsal midline incision is then made at the L5 and L6 level and the para-vertibral muscle groups are retracted bilaterally. L5 and L6 spinal nerves are then exposed, isolated, and tightly ligated with 6-0 silk suture. A sham operation is performed exposing the contralateral L5 and L6 spinal nerves as a negative control.

Tactile Allodynia:

Rats are transferred to an elevated testing cage with a wire mesh floor and allowed to acclimate for five to ten minutes. A series of Semmes-Weinstein monofilaments are applied to the plantar surface of the hindpaw to determine the animal's withdrawal threshold. The first filament used possesses a buckling weight of 9.1 gms (.96 log value) and is applied up to five times to see if it elicits a withdrawal response. If the animal has a withdrawal response then the next lightest filament in the series would be applied up to five times to determine if it could elicit a response. This procedure is repeated with subsequent lesser filaments until there is no response and the lightest filament that elicited a response is recorded. If the animal does not have a withdrawal response from the initial 9.1 gms filament then subsequent filaments of increased weight are applied until a filament elicits a response and this filament is then recorded. For each animal, three measurements are made at every time point to produce an average withdrawal threshold determination. Tests are performed prior to and at 1, 2, 4 and 24 hours post-drug administration. Tactile allodynia and mechanical hyperalgesia tests are conducted concurrently.

Mechanical Hyperalgesia:

Rats are transferred to an elevated testing cage with a wire mesh floor and allowed to acclimate for five to ten minutes.

A slightly blunted needle is touched to the plantar surface of the hindpaw causing a dimpling of the skin without penetrating the skin. Administration of the needle to control paws typically produces a quick flinching reaction, too short to be timed with a stopwatch and arbitrarily given a withdrawal time of 0.5 sec. The operated side paw of neuropathic animals exhibits an exaggerated withdrawal response to the blunted needle. A maximum withdrawal time of ten seconds is used as a cutoff time. Withdrawal times for both paws of the animals are measured three times at each time point with a five-minute recovery period between applications. The three measures are used to generate an average withdrawal time for each time point. Tactile allodynia and mechanical hyperalgesia tests are conducted concurrently.

The compounds may be tested for their neuroprotective activity after focal and global ischemia produced in rats or gerbils according to the procedures described in Buchan et al. (*Stroke*, Suppl. 148–152 (1993)) and Sheardown et al. (*Eur. J. Pharmacol.* 236:347–353 (1993)) and Graham et al. (*J. Pharmacol. Exp. Therap.* 276:1–4 (1996)).

The compounds may be tested for their neuroprotective activity after traumatic spinal cord injury according to the procedures described in Wrathall et. al. (*Exp. Neurology* 137:119–126 (1996)) and Iwasaki et. al. (*J. Neuro Sci.* 134:21–25 (1995)).

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular heteroaryl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the heteroaryl compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

1-[4-(4-Fluorophenoxy)phenyl]-3-methylpyrazole a) 4-(4-Fluorophenoxy)phenylhydrazine Hydrochloride:

A suspension of finely powdered 4-fluoro-4'-aminodiphenyl ether (2.00 g, 9.84 mmol) in 10 mL of water was cooled in an ice-water bath and 19.4 mL of conc. HCl was added dropwise via addition funnel. The resulting mixture was cooled to $-5°$ C. in an acetone-ice bath and a solution of sodium nitrite (crystalline; 0.714 g, 10.3 mmol) in 8 mL of cold water was added dropwise to the reaction at such a rate that the temperature remained between and $-5$ and $0°$ C. A solution of $SnCl_2 \cdot 2H_2O$ (6.66 g, 29.5 mmol) in 20 mL of conc. HCl at $-20°$ C. was treated with the reaction mixture added in portions, maintaining the temperature below $-10°$ C. A grey ppt. formed immediately and the resulting mixture was stirred at $-20°$ C. for 90 min. The solid was isolated by filtration and washed with cold EtOH (2×10 mL). The crude hydrazine, 2.36 g, was carried on without purification.

b) 1-[4-(4-Fluorophenoxy)phenyl]-3-methylpyrazole:

A suspension of the hydrazine (500 mg, 2.05 mmol) in 5.5 mL of 1:1 EtOH/water was treated with 300 μL (299 mg, 2.03 mmol) of 90% acetylacetaldehyde dimethylacetal and the resulting mixture was warmed with a heat gun for 2 min. The reaction was allowed to cool and extracted with hexane (4×10 mL). The pooled organic layers were washed with brine, dried ($Na_2SO_4$) and concentrated. The residue was subjected to column chromatography (silica gel, 10% EtOAc/heaxne) affording 134 mg (24%) of the title compound as a white solid, mp 80–81° C. $^1H$ NMR ($CDCl_3$): δ 7.74 (s, 1H), 7.58 (d, 2H, J 8.4 Hz), 7.06–6.95 (m, 6H), 6.23 (s, 1H), 2.37 (s, 3H).

EXAMPLE 2

1-(4-Phenoxyphenyl)-1H-pyrazole-3-carboxamide and 1-(4-phenoxyphenyl)-1H-pyrazole-5-carboxamide a) 3-Ethoxycarbonyl-1-(4-phenoxyphenyl)-1H-pyrazole and 5-ethoxycarbonyl-1-(4-phenoxyphenyl)-1H-pyrazole:

To a suspension of 4-phenoxyphenylboronic acid (1.70 g, 7.85 mmol), ethyl 3-pyrazolecarboxylate (0.55 g, 3.92 mmol), copper(II)acetate (1.1 g, 5.89 mmol) and 4 Å molecular sieves (powdered and heated at 200° C. for 2 h prior to use) in 30 mL of anhydrous THF was added 0.6 mL of pyridine. The reaction was stirred open to air at room temperature for 2 days and then filtered and the filtrate was concentrated to dryness. The crude product was purified by flash chromatography, eluting with 15% EtOAc/hexane, affording 5-ethoxycarbonyl-1-(4-phenoxyphenyl)-1H-pyrazole (Rf=0.6, 55 mg, 4.6%) and 3-ethoxycarbonyl-1-(4-phenoxyphenyl)-1H-pyrazole (Rf=0.5, 125 mg, 10.3%).

b) 1-(4-Phenoxyphenyl)-1H-pyrazole-3-carboxamide:

A solution of 3-ethoxycarbonyl-1-(4-phenoxyphenyl)-1H-pyrazole (120 mg, 0.39 mmol) in 5 mL of a 2N solution of ammonia in MeOH was stirred at rt for 4 d. TLC showed incomplete reaction and the solution was transferred to a sealed tube and heated at 70° C. overnight. The reaction was concentrated and purified by preparative TLC, eluting with 50% EtOAc/hexane, to yield 1-(4-phenoxyphenyl)-1H- pyrazole-3-carboxamide (Rf=0.26, 56 mg, 52%), mp 165–167° C. $^1$H NMR (300 MHz, DMSO-d$_6$) δ 8.50 (d, J=2.7 Hz, 1H, pyrazole), 7.92 (d, J=9.0 Hz, 2H, Phenyl), 7.71 (br, 1H, NH$_2$), 7.43 (m, 2H, Phenoxy), 7.39 (br, 1H, NH$_2$), 7.18 (m, 1H, Phenoxy), 7.17 (d, J 9.0 Hz, 2H, Phenyl), 7.07 (m, 2H, Phenoxy), 6.87 (d, J=2.7 Hz, 1H, pyrazole).

Starting with 5-ethoxycarbonyl-1-(4-phenoxyphenyl)-1H-pyrazole (50 mg, 0.16 mmol), the method described above gave 1-(4-phenoxyphenyl)-1H-pyrazole-5-carboxamide (25 mg, 55%), mp 142–144° C. $^1$H NMR (300 MHz, DMSO-d$_6$) δ 8.03 (br s, 1H, NH$_2$), 7.70 (d, J=1.8 Hz, 1H, pyrazole), 7.54 (br , 1H, NH$_2$), 7.42 (m, 2H, Phenoxy), 7.39 (d, J=9.0 Hz, 2H, Phenyl), 7.20 (m, 1H, Phenoxy), 7.08 (m, 2H, Phenoxy), 7.06 (d, J=9.0 Hz, 2H, Phenyl), 6.90 (d, J=1.8 Hz, 1H, pyrazole).

EXAMPLE 3

1-[4-(4-Nitrophenoxy)phenyl]-1H-[1,2,4]triazole

A mixture of 1-fluoro-4-nitrobenzene (0.17 mL, 1.6 mmol), 4-{[1,2,4]triazol-1-yl}phenol (0.26 g, 1.58 mmol), and potassium carbonate (1.69 g, 12.2 mmol) in DMF was refluxed overnight. The reaction was cooled to room temperature, then partitioned between water and ethyl acetate. The aqueous layer was extracted with ethyl acetate. The combined organic layers were washed with an aqueous sodium hydroxide solution (2N), water (2 times), dried over sodium sulfate, filtered, and evaporated under reduced pressure to give a yellow solid. Purification by column chromatography (silica gel; 1:1 hexane/ethyl acetate) and recrystallization from chloroform/hexane afforded 165 mg (37%) of the title compound as a yellow solid, mp 131–132° C. $^1$H-NMR (CDCl$_3$): δ 8.55 (s, 1H), 8.25 (d, J=9 Hz, 2H), 8.12 (s, 1H), 7.75 (d, J=9 Hz, 2H), 7.24 (d, J=9 Hz, 2H), 7.08 (d, J=9 Hz, 2H).

EXAMPLE 4

Anticonvulsant Activity of Compounds of the Invention

The ability of compounds of the present invention to block maximal electroshock-induced seizures (MES) is determined as described earlier.

A compound of the present invention is administered p.o. to mice 30 minutes before the test procedure. The compound exhibits protection against MES with an ED$_{50}$ (the dose provided protection of 50% of animals) of preferably below 10 mg/kg.

Activity of 1-(4-phenoxyphenyl)-1H-pyrazole-3-carboxamide as anticonvulsant, MES i.v. ED$_{50}$ in mouse 0.7 mg/kg. 1-[4-(4-Nitrophenoxy)phenyl]-1H-[1,2,4]triazole, MES po ED$_{50}$ 6.6 mg/kg. 1-(4-phenoxyphenyl)-1H-pyrazole-5-carboxamide, MES i.v. ED$_{50}$ 10.0 mg/kg.

EXAMPLE 5

Activity of Compound of the Invention as Sodium Channel Blocker

Compounds of the invention are tested in the electrophysiological and binding assays described above and produce dose-dependent inhibition of voltage-gated sodium currents recorded in HEK-293 cells stably expressing the rBIIA isoform of Na$^+$ channels. The blocking effect of preferrred compounds on Na$^+$ currents is highly sensitive to the holding voltage, indicating that the compounds bind to voltage-sensitive Na$^+$ channels in their inactivated states and have weak potency towards Na$^+$ channels in their resting states (Ragsdale et al., *Mol. Pharmacol.* 40:756–765 (1991); Kuo and Bean, *Mol. Pharmacol.* 46:716–725 (1994)). The apparent antagonist dissociation constant ($K_d$) of preferred compounds for inactivated sodium channels is less than 400 nM. 1-(4-Phenoxyphenyl)-1H-pyrazole-3-carboxamide was tested in rBIIA isoform of sodium channel and had Ki 0.35 µM.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound having the Formula I:

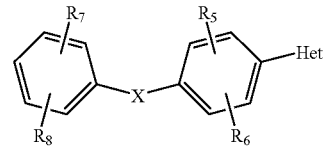

I or a pharmaceutically acceptable salt, prodrug or solvate thereof, wherein

X is one of O, S or CH$_2$;

Het is

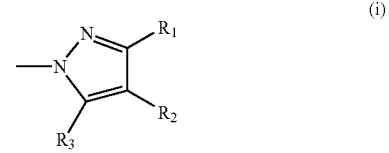

(i)

R$_1$ is selected from the group consisting of hydrogen, optionally substituted alkyl, heteroaryl optionally substituted with one or more groups independently selected from the group consisting of halo, halo(C$_{1-6}$)alkyl, hydroxy(C$_{1-6}$)alkyl, amino(C$_{1-6}$)alkyl, hydroxy, nitro, C$_{1-6}$ alkyl, C$_{1-6}$ alkoxy, aminocarbonyl, carbamoyloxy, C$_{1-6}$ alkylsulfonylamino, C$_{1-6}$ acyl and amino, C(O)R$_{10}$, CH$_2$C(O)R$_{10}$, S(O)R$_{10}$, and SO$_2$R$_{10}$;

R$_2$ and R$_3$ are independently selected from the group consisting of hydrogen, alkyl, alkenyl, alkynyl, aryl, cyano, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, aminosulfonyl, alkylaminosulfonyl, and alkylsulfonyl;

R$_5$, R$_6$, R$_7$, and R$_8$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkylthiol;

R$_{10}$ is selected from the group consisting of amino, alkyl, alkenyl, alkynyl, OR$_{11}$, alkylamino, dialkylamino, alkenylamino, dialkylaminoalkenyl, cycloalkyl, heterocycle, heteroaryl, aryl, aralkyl, arylalkenyl, arylalkynyl, and cycloalkylalkylamino, all of which are optionally substituted; and R$_{11}$ is selected from the group consisting of hydrogen, optionally substituted alkyl, and an alkalimetal.

2. A compound of claim 1, wherein R$_1$ is selected from the group consisting of an alkyl optionally substituted by halogen, hydroxy, carbamoyloxy, C$_{1-6}$ acyl, C$_{1-6}$ alkylsulfonylamino, aryl, or aminocarbonyl; C(O)R$_{10}$; CH$_2$C(O)R$_{10}$; or SO$_2$R$_{10}$, wherein R$_{10}$ is selected from the group consisting of C$_{1-6}$ alkyl, C$_{2-6}$ alkenyl, OR$_{11}$, amino, C$_{1-6}$ alkylamino, di(C$_{1-6}$)alkylamino, C$_{2-6}$ alkenylamino, heterocycle and mono- and di-(C$_{1-6}$)alkylaminoalkenyl, and R$_{11}$ is selected from the group consisting of hydrogen, optionally substituted alkyl, and an alkalimetal.

3. A compound of claim 2, wherein R$_{10}$ is selected from the group consisting of C$_{1-6}$ alkyl, C$_{2-6}$ alkenyl, OR$_{10}$, amino, C$_{1-6}$ alkylamino, di(C$_{1-6}$)alkylamino, C$_{2-6}$ alkenylamino, and di(C$_{1-6}$)alkylamino(C$_{2-6}$)alkenyl.

4. A compound of claim 3, wherein R$_2$ and R$_3$ are independently selected from the group consisting of hydrogen, C$_1$–C$_6$ alkyl, C$_2$–C$_6$ alkenyl, C$_2$–C$_6$ alkynyl, amino(C$_1$–C$_6$)alkyl, amino, C$_1$–C$_6$ alkylthio, cyano, C$_1$–C$_6$ alkylsulfinyl, hydroxy(C$_1$–C$_6$)alkyl, C$_1$–C$_6$ alkoxy, aminocarbonyl, C$_1$–C$_6$ alkylaminocarbonyl, C$_6$–C$_{10}$ arylaminocarbonyl, C$_6$–C$_{10}$ aryl(C$_1$–C$_6$) alkylaminocarbonyl, C$_1$–C$_6$ alkylcarbonylamino, C$_6$–C$_{10}$ arylcarbonylamino, and C$_6$–C$_{10}$ aryl(C$_1$–C$_6$) alkylcarbonylamino.

5. A compound of claim 3, wherein R$_2$ and R$_3$ are independently selected from the group consisting of hydrogen, C$_1$–C$_6$ alkyl, C$_1$–C$_6$ alkoxy, amino(C$_1$–C$_6$)alkyl, C$_1$–C$_6$ alkylthio and aminocarbonyl.

6. A compound of claim 1, wherein R$_5$, R$_6$, R$_7$, and R$_8$ are independently selected from the group consisting of hydrogen, halo, halo(C$_1$–C$_6$)alkyl, C$_1$–C$_6$ alkyl, hydroxy (C$_1$–C$_6$)alkyl, amino(C$_1$–C$_6$)alkyl, carboxy(C$_1$–C$_6$)alkyl, alkoxy(C$_1$–C$_6$)alkyl, nitro, amino, C$_1$–C$_6$ acylamino, amide, hydroxy, thiol, C$_1$–C$_6$ acyloxy, C$_1$–C$_6$ alkoxy, carboxy, carbonylamido and C$_1$–C$_6$ alkylthiol.

7. A compound of claim 1, wherein R$_1$ or R$_2$ is C(O)R$_{10}$ or SO$_2$R$_{10}$.

8. A compound of claim 7, wherein where R$_{10}$ is amino or C$_{1-6}$ alkyl.

9. A compound of claim 8, wherein X is O or S.

10. A compound of claim 9, wherein:

R$_5$ and R$_6$ are each hydrogen;

R$_3$ and R$_2$ are both H; and

R$_7$ and R$_8$ are selected from the group consisting of hydrogen, halo, halo(C$_1$–C$_6$)alkyl, C$_1$–C$_6$ alkyl, hydxoxy(C$_1$–C$_6$)alkyl, amino(C$_1$–C$_6$)alkyl, carboxy (C$_1$–C$_6$)alkyl, alkoxy(C$_1$–C$_6$)alkyl, nitro, amino, C$_1$–C$_6$ acylamino, amide, hydroxy, thiol, C$_1$–C$_6$ acyloxy, C$_1$–C$_6$ alkoxy, carboxy, carbonylamido and C$_1$–C$_6$ alkylthiol.

11. A compound of claim 1, wherein:

R$_1$ is C(O)R$_{10}$, CH$_2$C(O)R$_{10}$, or SO$_2$R$_{10}$;

X is O or S;

R$_{10}$ is amino, optionally substituted C$_1$–C$_6$ alkyl, or a heterocycle;

R$_2$, and R$_3$ are independently hydrogen, C$_1$–C$_6$ alkyl, C$_1$–C$_6$ alkylthio or C$_1$–C$_6$ alkylsulfinyl, R$_5$ and R$_6$ are as defined in claim 1, and R$_7$ and R$_8$ are independently selected from the group consisting of hydrogen, halo, halo(C$_1$–C$_6$)alkyl, C$_1$–C$_6$ alkyl, hydroxy(C$_1$–C$_6$)alkyl, amino(C$_1$–C$_6$)alkyl, carboxy(C$_1$–C$_6$)alkyl, alkoxy(C$_1$–C$_6$)alkyl, nitro, amino, C$_1$–C$_6$ acylamino, amide, hydroxy, thiol, C$_1$–C$_6$ acyloxy, C$_1$–C$_6$ alkoxy, carboxy, carbonylamido and C$_1$–C$_6$ alkyithiol.

12. A compound of claim 11, wherein R$_5$ and R$_6$ are both hydrogen.

13. A compound of Formula I:

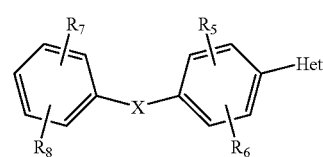

I or a pharmaceutically acceptable salt, prodrug or solvate thereof, wherein

X is O or S;

Het is

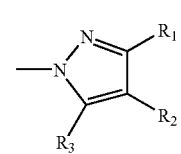

(i)

R$_1$ is C(O)R$_{10}$, CH$_2$C(O)R$_{10}$, or SO$_2$R$_{10}$ wherein R$_{10}$ is amino, all of which are optionally substituted;

R$_2$ and R$_3$ are independently hydrogen, C$_1$–C$_6$ alkyl, C$_1$–C$_6$ alkylthio or C$_1$–C$_6$ alkylsulfinyl; and R$_5$, R$_6$, R$_7$ and R$_8$ are independently selected from the group consisting of hydrogen, halo, halo(C$_1$–C$_6$)alkyl, C$_1$–C$_6$ alkyl, hydroxy(C$_1$–C$_6$)alkyl, amino(C$_1$–C$_6$) alkyl, carboxy(C$_1$–C$_6$)alkyl, alkoxy(C$_1$–C$_6$)alkyl, nitro, amino, C$_1$–C$_6$ acylamino, amide, hydroxy, thiol, C$_1$–C$_6$ acyloxy, C$_1$–C$_6$ alkoxy, carboxy, carbonylamido and C$_1$–C$_6$ alkylthiol.

14. A compound of Formula I:

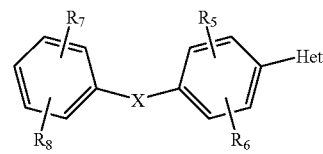

I or a pharmaceutically acceptable salt, prodrug or solvate thereof, wherein

X is O or S;

Het is

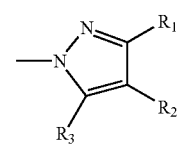

(i)

R$_1$ is C(O)R$_{10}$, wherein R$_{10}$ is amino, all of which are optionally substituted;

R$_2$ and R$_3$ are independently hydrogen, C$_1$–C$_6$ alkyl, C$_1$–C$_6$ alkylthio or C$_1$–C$_6$ alkylsulfinyl; and $R_5$, $R_6$, $R_7$ and $R_8$ are independently selected from the group consisting of hydrogen, halo, halo($C_1$–$C_6$)alkyl, $C_1$–$C_6$ alkyl, hydroxy($C_1$–$C_6$)alkyl, amino($C_1$–$C_6$)alkyl, carboxy($C_1$–$C_6$)alkyl, alkoxy($C_1$–$C_6$)alkyl, nitro, amino, $C_1$–$C_6$ acylamino, amide, hydroxy, thiol, $C_1$–$C_6$ acyloxy, $C_1$–$C_6$ alkoxy, carboxy, carbonylamido and $C_1$–$C_6$ alkylthiol.

15. A compound of claim 14, wherein X is O.

16. A compound having the Formula I:

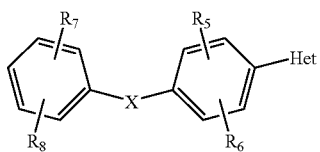

I or a pharmaceutically acceptable salt, prodrug or solvate thereof, wherein

X is $NR_9C(O)$ or $C(O)NR_9$, where $R_9$ is hydrogen or $C_1$–$C_{10}$ alkyl;

Het is

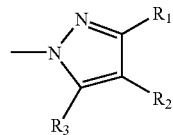

(i)

$R_1$ is $SO_2R_{10}$;

$R_2$ and $R_3$ are independently selected from the group consisting of hydrogen, alkyl, alkenyl, alkynyl, aryl, cyano, aminoalkyl, hydroxyalkyl, alkoxyalkyl, alkylthio, alkylsulfinyl, alkylsulfonyl, carboxyalkyl, alkylamino, dialkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, aminosulfonyl, alkylaminosulfonyl, and alkylsulfonyl;

$R_5$, $R_6$, $R_7$, and $R_8$ are independently selected from the group consisting of hydrogen, halo, haloalkyl, alkyl, alkenyl, alkynyl, hydroxyalkyl, aminoalkyl, carboxyalkyl, alkoxyalkyl, nitro, amino, ureido, cyano, acylamino, amide, hydroxy, thiol, acyloxy, azido, alkoxy, carboxy, carbonylamido and alkyithiol;

$R_{10}$ is selected from the group consisting of amino, alkyl, alkenyl, alkynyl, $OR_{11}$, alkylamino, dialkylamino, alkenylamino, dialkylaminoalkenyl, cycloalkyl, heterocycle, heteroaryl, aryl, aralkyl, arylalkenyl, arylalkynyl, and cycloalkylalkylamino, all of which are optionally substituted; and $R_{11}$ is selected from the group consisting of hydrogen, optionally substituted alkyl, and an alkalimetal.

17. A pharmaceutical composition, comprising the compound of any one of claims 1, 13, 14, or 16 and a pharmaceutically acceptable carrier.

18. A method of treating a disorder responsive to the blockade of sodium channels in a mammal suffering therefrom, comprising administering to a mammal in need of such treatment effective amount of the compound as claimed in any one of claims 1, 13, 14, or 16.

19. A method for treating or ameliorating neuronal loss following global and focal ischemia; treating or ameliorating neurodegenerative conditions; treating or ameliorating pain or tinnitus; treating or ameliorating manic depression; providing local anesthesia; treating arrhythmias, or treating convulsions, comprising administering to a mammal in need of such treatment an effective amount of the compound as claimed in any one of claims 1, 13, 14, or 16.

20. The method of claim 19, wherein the method is for treating or ameliorating pain and said pain is one of neuropathic pain, surgical pain or chronic pain.

21. A method of alleviating seizure activity in an animal subject, comprising administering to a mammal in need of such treatment an effective amount of a compound of anyone of claims 1, 13, 14, or 16.

* * * * *